United States Patent
Blackwood et al.

(10) Patent No.: US 7,174,272 B1
(45) Date of Patent: Feb. 6, 2007

(54) METHOD FOR DETECTING AN ELEMENT

(75) Inventors: Larry G. Blackwood, Idaho Falls, ID (US); Edward L. Reber, Idaho Falls, ID (US); Kenneth W. Rohde, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 11/304,850

(22) Filed: Dec. 14, 2005

(51) Int. Cl.
*G06F 19/00* (2006.01)

(52) U.S. Cl. .................... 702/179; 702/66; 702/67; 702/127; 702/172; 702/180; 702/181; 250/395

(58) Field of Classification Search .............. 702/179, 702/180, 181, 127, 172, 66, 67; 250/395
See application file for complete search history.

(56) References Cited

U.S. PATENT DOCUMENTS 6,791,089 B1 * 9/2004 Caffrey et al. ........... 250/358.1

* cited by examiner

*Primary Examiner*—Marc S. Hoff
*Assistant Examiner*—Phuong Huynh
(74) *Attorney, Agent, or Firm*—Wells St. John, P.S.

(57) ABSTRACT

A method for detecting an element is disclosed and which includes the steps of providing a gamma-ray spectrum which depicts, at least in part, a test region having boundaries, and which has a small amount of the element to be detected; providing a calculation which detects the small amount of the element to be detected; and providing a moving window and performing the calculation within the moving window, and over a range of possible window boundaries within the test region to determine the location of the optimal test region within the gamma-ray spectrum.

16 Claims, 2 Drawing Sheets

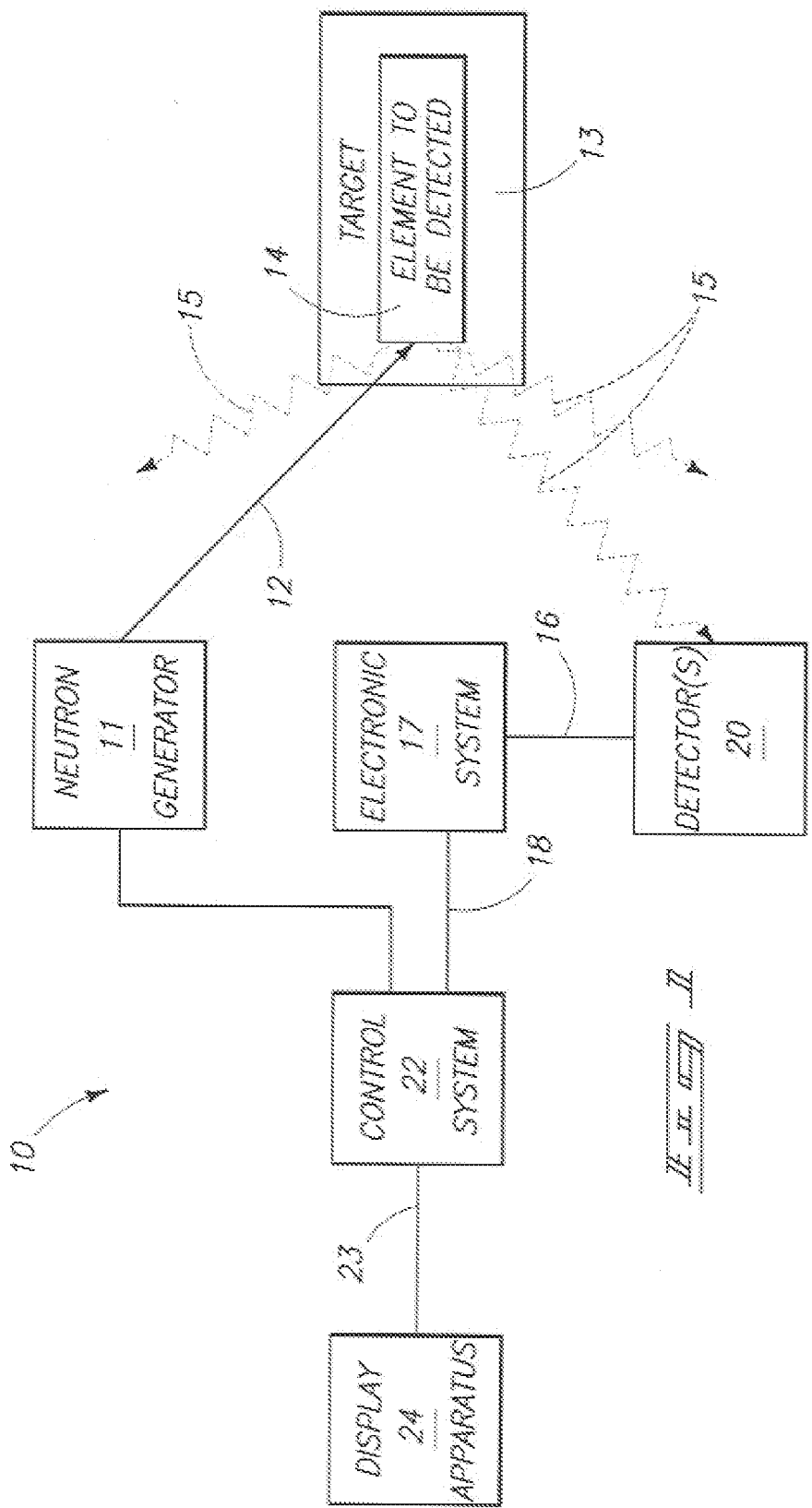

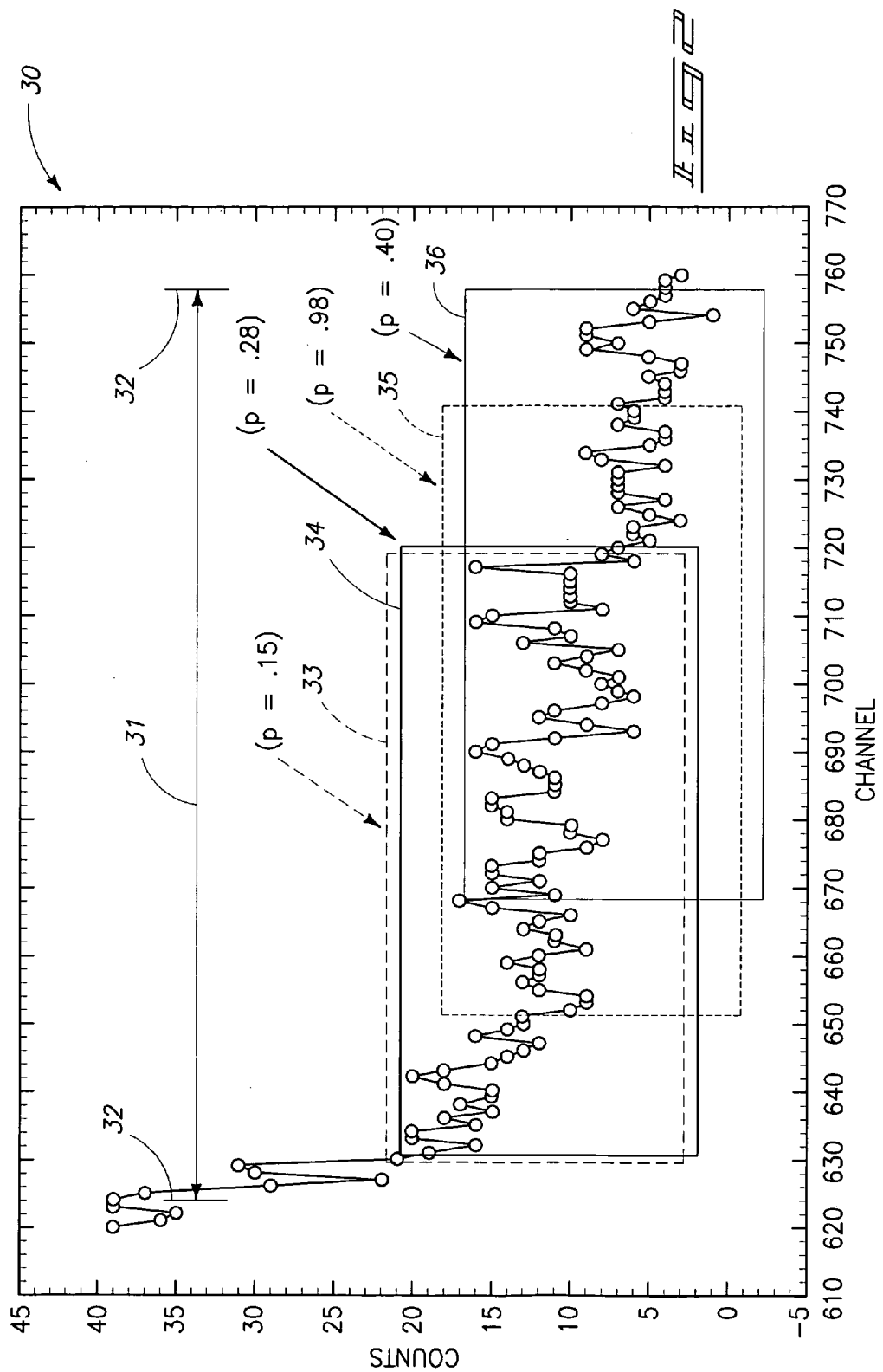

US 7,174,272 B1

METHOD FOR DETECTING AN ELEMENT

GOVERNMENT RIGHTS

The United States Government has certain rights in this invention pursuant to Contract No. DE-AC07-051D14517 between the United States Department of Energy and Battelle Energy Alliance, LLC.

TECHNICAL FIELD

The present invention relates to a method for detecting an element, and more specifically to a methodology which is utilized to improve the detection of small amounts of an element in a sodium iodide spectra, and which might be indicative of the presence of contraband such as explosives and the like.

BACKGROUND OF THE INVENTION

As of late, various methodologies and devices have been developed or are currently under development for the detection of explosives, and other contraband of various quantities, and which might be utilized in terrorist acts. Currently, vehicles and containers entering restricted areas such as military bases, courtrooms and facilities for public transportation are checked for contraband by means of physical search, x-ray, vapor detection or canine units who are deployed by law enforcement or other military personnel. Heretofore, various automatic spectral analysis routines have been developed and which are useful in the detection of explosives which might be concealed on vehicles, containers and the like. Such systems have included methodology and apparatus for interrogating a vehicle or container with neutrons provided by a neutron generator and thereafter collecting the gamma energy generated by the presence of any explosive substance by utilizing sodium iodide detectors. In these earlier devices and methodology, the typical gamma-ray spectrum collected was then analyzed based upon Gaussian peak fitting including peak deconvolution in order to identify the explosive substance. While the methodology and devices utilized heretofore have worked with some degree of success, they have had shortcomings which have detracted from their usefulness. More specifically, the methodology as discussed above has not produced reliable results when the sodium iodide spectra is collected from measurements of relatively small quantities of material at increasing stand-off distances. Further, it should be understood that some gamma-ray spectra contain ill-defined peaks for certain chemical elements of interest. A primary example of this are the typical weak, high energy peaks such as those used for the detection of nitrogen in spectra obtained from sodium iodide detectors and which would indicate the presence of an explosive. With regard to these energy peaks, they typically are broad and often overlap. The poor peak resolution combined with the low number of counts available when attempting to identify small elemental quantities producing these weak peaks make it difficult to determine accurate peak widths, and peak region boundaries in any spectra. These same conditions also make energy calibrations less precise so that there may be considerable uncertainty in properly centering regions of interest based upon an energy range surrounding energies for known gamma-rays. Under these conditions, identifying the optimal region boundaries for summing, Gaussian peak fitting or other methods of elemental detection becomes quite difficult. Those skilled in the art understand that if the region boundaries are not often optimally defined, the detection capabilities for small amounts of materials will be significantly degraded.

Therefore, a method for detecting an element which avoids the shortcomings attendant with the prior art methodology and devices utilized heretofore is the subject matter of the present application.

SUMMARY OF THE INVENTION

A first aspect of the present invention relates to a method for detecting an element, and which includes the steps of providing a gamma-ray spectrum which depicts, at least in part, a test region having boundaries, and which has a small amount of the element to be detected; providing a calculation which detects the small amount of the element to be detected; and providing a moving window and performing the calculation within the moving window, and over a range of possible window boundaries within the test region to determine the location of the optimal test region within the gamma-ray spectrum.

Another aspect of the present invention relates to a method for detecting an element, and which includes the steps of providing a gamma-ray spectrum which depicts a region of interest, with boundaries, and having a small amount of an element to be detected; providing a calculation of the probability of detection of the small amount of the element within the gamma-ray spectrum and which produces a detection value; defining a moving window within the region of interest, and wherein the calculation of the probability of detection of the small amount of the element is performed each time the window is moved within the region of interest; and selecting an optimal window location which provides a maximum detection value for the probability of detection of the small amount of the element to be detected.

These and other aspects of the present invention will be described in greater detail hereinafter.

BRIEF DESCRIPTION OF THE DRAWINGS

Preferred embodiments of the invention are described below with reference to the following accompanying drawings.

FIG. 1 is a greatly simplified schematic diagram of an arrangement which is useful for practicing the methodology of the present invention.

FIG. 2 is a graphical depiction showing an example of a typical section of a sodium iodide spectrum and illustrating features of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The present invention provides a method for detecting an element and which, in some applications, might indicate the presence of contraband such as an explosive. It should be understood that the present invention is not limited to this purpose, but may be found useful in detection of trace or large amounts of different elements which indicates the presence of other materials which may be of interest to a variety of law enforcement personnel.

FIG. 1 shows a greatly simplified depiction of a system or an arrangement 10 which is useful in practicing the methodology of the present invention. Broadly speaking, the method for detecting an element of the present invention includes the steps of providing a gamma-ray spectrum which depicts, at least in part, a test region having boundaries, and which has a small amount of the element to be detected; providing a calculation which detects the small amount of the element to be detected; and providing a moving window and performing the calculation within the moving window, and over a range of possible window boundaries within the test region to determine the location of the optimal test region within the gamma-ray spectrum. The present methodology provides a novel means by which an operator can detect small quantities of an element of interest with a high level of detection confidence and with a low level of false positives. Additionally, the present methodology allows a system to be built which utilizes considerably fewer sodium iodine detectors that will be described below and which will operate with quicker through-put while maintaining a high level of detection confidence.

Referring to FIG. 1, it will be seen that an apparatus for detecting an element and which can be utilized in the methodology of the present invention is generally indicated by the numeral 10. The present apparatus which is shown in a very general, and simple schematic fashion includes, as a general matter, a neutron generator 11 which is operable to generate a source or stream of neutrons 12 which are directed towards or travel in the direction of a target to be interrogated 13. As seen, the target to be interrogated includes trace amounts of an element to be detected 14. This trace amount of an element to be detected may include elements such as nitrogen which forms an important part of most modern explosives. As should be understood, the neutron generator may be commercially purchased. A commercially suitable neutron generator is a JENIE™ 16-C neutron generator which is available from Sodern, 20 Descartes Avenue, Limeil, Breveannes, France. Other commercially available neutron generators could also be employed. In the illustrated embodiment, 14 MeV neutrons are produced. In this regard, the high energy neutrons penetrate the target 13 to be interrogated, and interact with any trace amounts of explosive which might include nitrogen which is in or on the target. Some of these neutrons are then thermalized within the trace amounts of the element to be detected or surrounding material and are captured by the nitrogen atoms which are present. More specifically, some of the neutrons inelastically scatter off of the various trace elements until they eventually thermalize and are captured. These interactions release signature gamma-rays 15 which are received, and are substantially measured by a gamma-ray energy detector 20 which typically comprises a sodium iodine detector. Typically, the arrangement 10 will have an array of gamma-ray energy detectors 20. As should be understood, when a neutron is captured by a nitrogen atom that might be incorporated, for example, on an explosive, a 10.8 MeV gamma-ray of energy is released. The gamma-ray energy detector 20 receives this energy and produces an electrical signal output 16 which is then subsequently supplied to a digital electronic system 17 of conventional design. The digital electronic system 17 is operable to generate a gamma-ray spectrum 30 from the received electrical output 16 and further produces an electrical signal output 18 which is supplied to a control system 22. The control system is operable to analyze a resulting gamma-ray spectrum 30 as seen in FIG. 2 from the received electrical output 18 and is further able to supply a corresponding electrical signal 23 to a display apparatus which provides a message to an operator and which indicates the presence of the element 14 to be detected. The control system may implement other methodology for detecting the small amount of the element to be detected including providing non-parametric assumptions about a shape of the gamma-ray spectrum in a region of interest and which would indicate the presence of the element to be detected; and applying a statistical test to the shape of the gamma-ray spectrum based upon the non-parametric assumptions to detect the small amount of the element to be detected.

Therefore the methodology of the present invention includes the steps of providing a neutron generator 11 which provides a source of neutron energy 12, interrogating a target 13 with the neutron energy; providing a gamma-ray energy detector 20 which has an electrical output 16; collecting the gamma-ray radiation 15 which is emitted by the target 13 following the interrogation of the target with the neutron energy with the gamma-ray energy detector; and receiving the electrical output 60 of the gamma-ray energy detector to form the gamma-ray spectrum 30 as seen in FIG. 2.

Referring now to FIG. 2, the method for detecting an element of the present invention includes a first step of providing a gamma-ray spectrum 30 which depicts, at least in part, a test region 31 having boundaries 32, and which has a small amount of the element to be detected. This methodology includes another step of providing a calculation which detects the small amount of the element to be detected and which will be discussed below. Still further, the methodology includes the step of providing a moving window 33–36 and performing the calculation within the moving window, and over a range of possible window boundaries within the test region 31 to determine the location of the optimal test region within the gamma-ray spectrum. With respect to the methodology as described above, the calculation which detects the small amount of the element detected is a probability detection which is designated as "p" in FIG. 2. The maximum p-value for the example depicted in FIG. 2 is that seen in the window which is labeled 35. In the methodology as described above, the step of providing a moving window further includes the step of varying the range over which the window 33–36 is moved based, at least in part, upon the nature of the gamma-ray spectrum 30 provided, and the probability calculation for the small amount of the element to be detected.

In the methodology of the present invention, the step of providing a moving window includes a further step of selecting a starting channel for the test region 31; and selecting an initial window width based, at least in part, upon the width of the test region 31 and which is characterized by a plurality of channels. The moving window width as seen and which is illustrated as windows 31–36, respectively, is equal to 90 channels. As seen in FIG. 2, the methodology includes varying the range over which the window is moved, based in part upon the nature of the gamma-ray spectrum provided and the probability calculation for the small amount of element to be detected. As seen in FIG. 2, the window is illustrated in four locations, that being at 33, 34, 35, and 36, respectively. In the methodology as described, the method further includes a step of selecting a starting channel for the test region, and selecting an initial window width, here illustrated as 90 channels, based, at least in part upon, the width of the test region 31 and which is characterized by a plurality of channels; and selecting a range of values for the moving window starting channel, and the width of the window, respectively. As seen herein, the test region width is 628 channels, and the range over which the window starting point is allowed to vary equals 41 channels. In this example, a measure of the detection probability for the element to be detected is calculated for the data in 41 different windows. However, only four windows 33–36 are shown in FIG. 2 in order to provide a clear understanding of the present invention. The measure of detection as provided for in the present methodology and as seen in FIG. 2, comprises a probability value associated with the measure of detection for an element of interest such as nitrogen. This is designated as p in FIG. 2. After the step of selecting a measure of detection for the small amount of the element to be detected, the methodology includes another step of selecting a window having a predetermined width value as defined by a plurality of channels, and which resides within the range of values selected for the starting channel, and the predetermined window width. The method includes another step of calculating the measure of detection (here p) for the small amount of the element to be detected within the selected window to provide a first detection value. As seen in each of the respective windows 33–36, the probability of detection is given a value. For example, the first window 33 has a probability value of 0.15; the second window has a probability value of 0.28, the third window 0.98; and the fourth window 0.40. In the present methodology, after the step of calculating the measure of detection to provide a first detection value (for example, 0.15), the method includes the step of moving the window at least one channel while maintaining the same predetermined window width; and recalculating the measure of detection for the small amount of the element to be detected to provide a second detection value. Still further, the method includes another step after the step of calculating the measure of detection to provide a second detection value, of repeating the earlier step of moving the window one channel while maintaining the same predetermined window width, and recalculating the measure of detection for the small amount of the element to be detected to provide a plurality of discrete detection values. As seen in FIG. 2, four windows are shown for illustration each having a different detection value indicated by p.

In the methodology as described, after the step of repeatedly removing the window 33–36 over each channel within the range of values selected for the test region 31, the method further includes the steps of calculating an N-point moving average of the plurality of detection values; and selecting the maximum moving average value for the final detection value. In the present methodology, after the step of selecting the maximum moving average value for the detection value, the method further comprises a step of increasing the width of the window by one channel, and after the step of increasing the window width, repeating the earlier mentioned steps, those being, providing a detection value for the window, and then moving the window one channel while maintaining the same window width, and recalculating the measure of detection for the small amount of the element to be detected to provide a second value. This methodology is repeated until every possible width value within the test region 31 has been tested. Thereafter, the methodology includes the step of selecting a maximum detection value as a final detection value for the small amount of the element to be detected. In the methodology as described, the method further includes the steps of translating the maximum detection values into measures of a probability detection and/or a detection confidence; and adjusting the measures of the probability of detection and/or detection confidence to reduce the probability of providing a false final detection value which would indicate the presence of the small amount of element to be detected. In the methodology as described, the step of selecting an estimated starting channel and test region width for use in the present methodology is based, at least in part, upon a consideration of a estimated peak centroid location and peak width value for the element to be detected.

In the methodology as described herein, the gamma-ray spectrum is selected from the group comprising individual and/or summed gamma-ray spectra. Still further, the measure of detection for the gamma-ray spectrum comprises a plurality of measures and detection.

Operation

The operation of the described embodiment of the present invention is believed to be readily apparent and is briefly summarized at this point.

The present methodology for detecting an element of the present invention is best understood by a study of FIGS. 1 and 2. As shown therein, the methodology includes a first step of providing a gamma-ray spectrum 30 which depicts a region of interest 31 with boundaries 32, and having a small amount of an element to be detected. Further the method includes the step of providing a calculation of the probability of detection of the small amount of the element within the gamma-ray spectrum and which produces a detection value. This is indicated by the value p in FIG. 2. Further, the methodology includes the step of defining a moving window 33–36 within the region of interest, and wherein the calculation of the probability of detection of the small amount of the element is performed each time the window is moved within the region of interest 31. As seen in FIG. 2, the window is shown in four different locations indicated by the numbers 33, 34, 35, and 36, respectively. Still further, the method includes a step of selecting an optimal window location which provides a maximum detection value for the probability of detection of the small amount of the element to be detected. As seen in FIG. 2, this is illustrated by the window labeled 35 and which has a detection value of probability equal to 0.98.

In the methodology as described above, the method includes further steps of selecting a predetermined width for the moving window within the region of interest. As illustrated in FIG. 2, the width of the moving window is 90 channels, however, varying widths may be provided based upon the spectra which has been supplied. As noted in the earlier discussion, each time the window is moved, a different probability of detection is calculated. Therefore, the method of the present invention further includes another step of calculating an n-point moving average of the detection values which are provided after the window is moved. In the methodology as described and before the step of selecting an optimal window location, the method includes another step of increasing the predetermined width for the moving window; moving the window again within the region of interest; and calculating the probability of detection of the small amount of the element to be detected each time the window is moved to provide a detection value. In the methodology as described, the step of increasing the predetermined width of the window occurs repeatedly until all possible width values of the region of interest 31 has been tested. Further, in the present methodology, the step of selecting an optimal window location further includes the step of selecting a maximum detection value as a final detection value for the small amount of the element to be detected.

Therefore it will be seen that the present methodology as described above is useful, when applied to a gamma-ray spectrum to detect small amounts of elements which may indicate the presence of contraband substance such as explosives in concealed locations within containers, vehicles and the like.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A method for detecting an element, comprising:
providing a gamma-ray spectrum which depicts, at least in part, a test region having boundaries, and which has a small amount of the element to be detected;
providing a calculation which detects the small amount of the element to be detected;
providing a moving window and performing the calculation within the moving window, and over a range of possible window boundaries within the test region to determine the location of an optimal test region within the gamma-ray spectrum and to provide a plurality of detection values for the element to be detected;
calculating the n-point moving average of the plurality of detection values; and
selecting the maximum moving average value as the final detection value for the small amount of the element to be detected; and displaying a message indicating the presence of the element to be detected.

2. A method as claimed in claim 1, and wherein the calculation which detects the small amount of the element to be detected is a probability calculation.

3. A method as claimed in claim 2, and wherein the step of providing a moving window further comprises:
varying the range over which the window is moved, based, at least in part, upon the nature of the gamma-ray spectrum provided, and the probability calculation for the small amount of the element to be detected.

4. A method for detecting an element, comprising:
providing a gamma-ray spectrum which depicts, at least in part, a test region having boundaries, and which has a small amount of the element to be detected;
providing a calculation which measures the detection for a small amount of the element to be detected;
providing a moving window;
selecting a starting channel for the test region;
selecting an initial window width of the moving window based, at least in part, upon the width of the test region and which is characterized by a plurality of channels;
selecting a range of values for the moving window starting channel, and the width of the moving window, respectively;
selecting a measure of detection for the small amount of the element to be detected;
after the step of selecting the measure of detection, selecting a moving window having a predetermined width value as defined by a plurality of channels, and which resides within the range of values selected for the starting channel, and the predetermined moving window width;
calculating the measure of detection for the small amount of the element of interest within the selected window to provide a first detection value;
after the step of calculating the measure of detection to provide a first detection value, moving the window one channel while maintaining the same predetermined window width, and recalculating the measure of detection for the small amount of the element to be detected to provide a second detection value; and
after the step of calculating the measure of detection to provide a second detection value, repeating the step of moving the window one channel while maintaining the same predetermined window width, and recalculating the measure of detection for the small amount of the element to be detected to provide a plurality of discrete detection values.

5. A method as claimed in claim 4, and wherein after the steps of repeatedly moving the window over each channel within the range of values selected for the test region, the method further comprises:
calculating an N-point moving average of the plurality of detection values; and
selecting the maximum moving average value for the final detection value; and displaying a message indicating the presence of the element to be detected.

6. A method as claimed in claim 5, and after the step of selecting the maximum moving average value for the detection value, the method further comprises:
increasing the width of the window by one channel, and after the step of increasing the window width, repeating the steps of claim 5.

7. A method as claimed in claim 6, and further comprising:
repeating the steps of claim 6 until every possible width value within the test region has been tested; and
selecting a maximum detection value as a final detection value for the small amount of the element of interest to be detected.

8. A method as claimed in claim 4, and wherein the gamma-ray spectrum is selected from the group comprising individual and/or summed gamma-ray spectra.

9. A method as claimed in claim 4, and wherein the measure of detection comprises a plurality of measures of detection.

10. A method as claimed in claim 7, and further comprising:
translating the maximum detection values into measures of a probability of detection and/or a detection confidence; and
adjusting the measures of the probability of detection and/or detection confidence to reduce the probability of providing a false final detection value which would indicate the presence of the small amount of the element to be detected.

11. A method as claimed in claim 4, and wherein the step of selecting an estimated starting channel and test region width is based, at least in part, upon a consideration of a estimated peak, centroid location and peak width value for the element to be detected.

12. A method for detecting an element, comprising:
providing a gamma-ray spectrum which depicts a region of interest, with boundaries, and having a small amount of an element to be detected;
providing a calculation of a probability of detection of the small amount of the element within the gamma-ray spectrum and which produces a detection value;
defining a moving window within the region of interest, and wherein the calculation of the probability of detection of the small amount of the element is performed each time the window is moved within the region of interest;

selecting a predetermined width for the moving window within the region of interest;

selecting an optimal window location which provides a maximum detection value for the probability of detection of the small amount of the element to be detected; and calculating an n-point moving average of the detection values which are provided after the moving window is moved and displaying a message indicating the presence of the element to be detected.

13. A method as claimed in claim 12, and further comprising:

providing a target to be interrogated;

providing a neutron generator which provides a source of neutron energy, and further interrogating the target with the neutron energy;

providing a gamma-ray energy detector which has an electrical output, and collecting gamma-ray radiation which is emitted by the target following the interrogation of the target with the neutron energy with the gamma-ray energy detector; and receiving the electrical output of the gamma-ray energy detector to form the gamma-ray spectrum.

14. A method as claimed in claim 12, and wherein before the step of selecting an optimal window location, the method further comprises:

increasing the predetermined width for the moving window;

moving the window again within the region of interest; and calculating the probability of detection of the small amount of the element to be detected each time the window is moved to provide a detection value.

15. A method as claimed in claim 14, and wherein the step of increasing the predetermined width of the moving window occurs repeatedly until all possible width values of the region of interest has been tested.

16. A method as claimed in claim 15, and wherein the step of selecting an optimal window location further comprises:

selecting a maximum detection value as a final detection value for the small amount of the element to be detected.

* * * * *